United States Patent [19]

Richter

[11] 4,053,297

[45] Oct. 11, 1977

[54] SELECTIVE HERBICIDAL COMPOSITIONS

[75] Inventor: Sidney B. Richter, Chicago, Ill.

[73] Assignee: Velsicol Chemical Corporation, Chicago, Ill.

[21] Appl. No.: 570,125

[22] Filed: Apr. 21, 1975

[51] Int. Cl.$^2$ .................. A01N 9/28; A01N 9/12; A01N 9/22
[52] U.S. Cl. .................................. 71/88; 71/90; 71/118
[58] Field of Search .................... 71/118, 88, 90

[56] References Cited

FOREIGN PATENT DOCUMENTS 2,402,983  8/1974  Germany .................. 71/88

*Primary Examiner*—Lewis Gotts
*Assistant Examiner*—Catherine L. Mills
*Attorney, Agent, or Firm*—Robert J. Schwarz; Dietmar H. Olesch

[57] ABSTRACT

This invention discloses herbicidal compositions which selectively destroy weeds in cereal grain without damaging said grain plants, comprising in combination an anilide of the formula

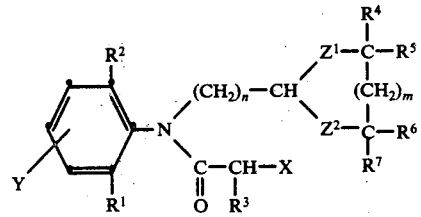

wherein Y is selected from the group consisting of hydrogen, lower alkyl and halogen; $R^1$ is selected from the group consisting of hydrogen, lower alkyl and lower alkoxy; $R^2$ is lower alkyl; $R^3$ is selected from the group consisting of hydrogen and lower alkyl; X is halogen; $n$ is an integer from 1 to 2; $Z^1$ and $Z^2$ are independently selected from the group consisting of oxygen and sulfur; $R^4$, $R^5$, $R^6$, and $R^7$ are independently selected from the group consisting of hydrogen and lower alkyl; and $m$ is an integer from 0 to 2; and from 0.01 to 15.0 weight percent of said anilide of a compound of the formula

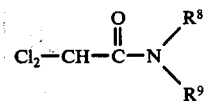

wherein $R^8$ and $R^9$ are each selected from the group consisting of alkyl, alkenyl, alkynyl, haloalkyl, haloalkenyl, haloalkynyl, alkoxyalkyl, halogen-substituted alkoxyalkyl, alkenyloxyalkyl, halogen-substituted alkenyloxyalkyl, cycloalkyl and cyanoalkyl; and wherein $R^8$ and $R^9$ together with the nitrogen atom can form a 5- to 7-membered heterocyclic ring which optionally contains an additional heteroatom and which optionally is substituted with alkyl.

5 Claims, No Drawings

SELECTIVE HERBICIDAL COMPOSITIONS

A vast number of herbicides are disclosed in the literature purporting to be useful in agriculture. However, too many of these compositions are insufficiently selective in that they indiscriminately destroy crops as well as undesired vegetation. Among such herbicides which frequently lack selectivity are the class of herbicides known as α-haloacetanilides, including their higher homologs.

It has now been found that a certain subclass of α-haloacetanilides, i.e., those having heterocyclic substituents on the nitrogen atom, can be rendered safer to cereal grains, including corn, without affecting their herbicidal activity against weeds commonly encountered in the culture of such grains, by combining them in certain proportions with α,α-dichloroalkanamides, as will hereinafter be described.

Thus, one embodiment of the present invention resides in a herbicidal composition which selectively destroys weeds growing in cereal grain cultures without damaging said cereal grain plants, comprising in combination an anilide of the formula

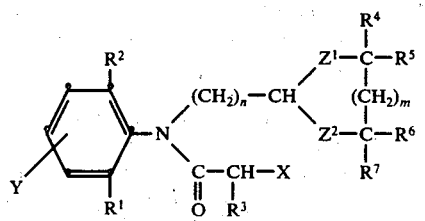

(I)

wherein Y is selected from the group consisting of hydrogen, lower alkyl and halogen; $R^1$ is selected from the group consisting of hydrogen, lower alkyl and lower alkoxy; $R^2$ is lower alkyl; $R^3$ is selected from the group consisting of hydrogen and lower alkyl; X is halogen; $n$ is an integer from 1 to 2; $Z^1$ and $Z^2$ are independently selected from the group consisting of oxygen and sulfur; $R^4$, $R^5$, $R^6$, and $R^7$ and are independently selected from the group consisting of hydrogen and lower alkyl; and $m$ is an integer from 0 to 2; and from about 0.01 percent by weight to about 15.0 percent by weight of said anilide of a compound of the formula

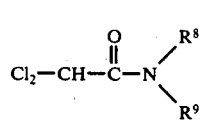

(II)

wherein $R^8$ and $R^9$ are each selected from the group consisting of alkyl, alkenyl, alkynyl, haloalkyl, haloalkenyl, haloalkynyl, alkoxyalkyl, halogen-substituted alkoxyalkyl, alkenyloxyalkyl, halogen-substituted alkenyloxyalkyl, cycloalkyl and cyanoalkyl; and wherein $R^8$ and $R^9$ together with the nitrogen atom can form a 5- to 7-membered heterocyclic ring which optionally contains an additional heteroatom and which optionally is substituted with alkyl.

In a preferred embodiment of the present invention the variable moieties of the amides of formula II are more restrictively defined in that $R^8$ and $R^9$ are each selected from the group consisting of lower alkyl, lower alkenyl, lower alkynyl, lower chloroalkyl, lower bromoalkyl, lower chloroalkenyl, lower alkoxyalkyl, chlorine- or bromine-substituted lower alkoxyalkyl, lower alkenyloxyalkyl, cycloalkyl of from 3 to 7 carbon atoms; and $R^8$ and $R^9$ together with the nitrogen atom can form a 5- to 7-membered heterocyclic ring which optionally contains as an additional heteroatom an oxygen atom and which can be optionally substituted with lower alkyl.

The term lower as used herein designates a straight or branched carbon chain of up to 6 carbon atoms.

In a most preferred embodiment of this invention the $R^8$ and $R^9$ moieties in the compounds of formula II are allyl or lower alkyl or together form an oxazolidine ring which can be substituted with one or two methyl groups in the 2-position.

The anilides of formula I are known in the art and examples of these compounds are N-α-chloroacetyl-N-(1,3-dioxolan-2-ylmethyl)-2,6-dimethylaniline, N-α-chloroacetyl-N-(1,3-dioxolan-2ylmethyl)-2,6-diethylaniline, N-α-chloroacetyl-N-(1,3-dioxolan-2-ylmethyl)-2,6-dipropylaniline, N-α-chloroacetyl-N-(1,3-dioxolan-2-ylmethyl)-2,6-dibutylaniline, N-α-chloroacetyl-N-(1,3-dioxolan-2-ylmethyl-2,6-dipentylaniline, N-α-chloroacetyl-N-(1,3-dioxolan-2-ylmethyl)-2,6-dihexylaniline, N-α-chloroacetyl-N-(1,3-dioxolan-2-ylmethyl)-2-methyl-6-ethylaniline, N-α-chloroacetyl-N-(1,3-dioxolan-2-ylmethyl)-2-methyl-6-methoxyaniline, N-α-chloroacetyl-N-(1,3-dioxolan-2-ylmethyl)-2-methyl-6-ethoxyaniline, N-α-chloroacetyl-N-(1,3-dioxolan-2-ylmethyl)-2-methyl-6-hexyloxyaniline, N-α-chloroacetyl-N-(1,3-dioxolan-2-ylmethyl)-2-ethyl-4-chloroaniline, N-α-chloroacetyl-N-(1,3-dioxolan-2-ylmethyl)-2-ethyl-3-methylaniline, N-α-chloroacetyl-N-(1,3-dioxolan-2-ylmethyl)-2-ethyl-4-bromoaniline, N-α-chloroacetyl-N-(1,3-dioxolan-2-ylmethyl)-2-ethyl-4-fluoroaniline, N-α-chloroacetyl-N-(1,3-dioxolan-2-ylmethyl)-2-ethylaniline, N-α-chloroacetyl-N-(1,3-dioxolan-2-ylmethyl)-2-methylaniline, N-α-chloroacetyl-N-(1,3-dioxolan-2-ylmethyl)-2-propylaniline, N-α-chloropropionyl-N-(1,3-dioxolan-2-ylethyl)-2,6-diethylaniline, N-α-bromopropionyl-N-(1,3-dioxolan-2-ylmethyl)-2,6-diethylaniline, N-α-bromoacetyl-N-(1,3-dioxolan-2-ylmethyl)-2,6-diethylaniline, N-α-chlorobutanoyl-N-(1,3-dioxolan-2-ylmethyl)-2,6-diethylaniline, N-α-chloropentanoyl-N-(1,3-dioxolan-2-ylmethyl)-2,6-diethylaniline, N-α-chloroacetyl-N-(1,3-dioxan-2-ylmethyl)-2,6-diethylaniline, N-α-chloroacetyl-N-(1,3-dioxan-2-ylmethyl)-2,6-dimethylaniline, N-α-chloroacetyl-N-(1,3-dioxan-2-ylmethyl)-2,6-dipropylaniline, N-α-chloroacetyl-N-(1,3-dioxan-2-ylmethyl)-2-methyl-4-chloroaniline, N-α-chloroacetyl-N-(1,3-dioxan-2-ylmethyl)-2,4,6-trimethylaniline, N-α-chloroacetyl-N-(1,3-dioxan-2-ylmethyl)-2-methyl-4-fluoroaniline, N-α-chloroacetyl-N-(1,3-dioxan-2-ylmethyl)-2-ethyl-6-methoxyaniline, N-α-chloropropionyl-N-(1,3-dioxan-2-ylethyl)-2,6-diethylaniline, N-α-bromoacetyl-N-(1,3-dioxan-2-ylmethyl)-2,6-diethylaniline, N-α-chlorobutanoyl-N-(1,3-dioxan-2-ylmethyl)-2,6-diethylaniline, N-α-chloropentanoyl-N-(1,3-dioxan-2-ylmethyl)-2,6-diethylaniline, N-α-chlorohexanoyl-N-(1,3-dioxan-2-ylmethyl)-2,6diethylaniline, N-α-chloroacetyl-N-(1,3-dioxepan-2-ylmethyl)-2,6-dimethylaniline, N-α-chloroacetyl-N-(1,3-dioxepan-2-ylmethyl)-2,6-diethylaniline, N-α-chloroacetyl-N-(1,3-dioxepan-2-ylmethyl)-2,6-dipropylaniline, N-α-chloroacetyl-N-(1,3-dioxepan-2-ylmethyl)-2,6-dihexylaniline, N-α-chloroacetyl-N-(1,3-dioxepan-2-ylmethyl)-2-methyl-4-chloroaniline, N-α-chloroacetyl-N-(1,3-dioxepan- 2- ylmethyl)-2-ethyl-4-fluoroaniline, N-α-chloroacetyl-N-(1,3-dioxepan-2-ylmethyl)-2-ethyl-3-butylaniline, N-α-chloroacetyl-N-(1,3-dioxepan-2-ylmethyl)-2,4,6-triethylaniline, N-α-chloroacetyl-N-(1,3-dioxepan-2-ylmethyl)-2-ethyl-6-methoxyaniline, N-α-chloroacetyl-N-(1,3-dioxepan-2-ylmethyl)-2,6-diethyl-4-bromoaniline, N-α-bromoacetyl-N-(1,3-dioxepan-2-ylmethyl-2,6-diethylaniline, N-α-chloropropionyl-N-(1,3-dioxepan-2-ylmethyl)-2,6-diethylaniline, N-α-bromopropionyl-N-(1,3-dioxepan-2-ylmethyl)-2,6-diethylaniline, N-α-chlorobutanoyl-N-(1,3-dioxepan-2-ylethyl)-2,6-diethylaniline, N-α-chloropentanoyl-N-(1,3-dioxepan-2-ylethyl)-2,6-diethylaniline, N-α-chloroacetyl-N-(4-methyl-1,3-dioxolan-2-ylmethyl)-2,6-diethylaniline, N-α-chloroacetyl-N-(4-ethyl-1,3-dioxolan-2-ylmethyl)-2,6-diethylaniline, N-α-chloroacetyl-N-(4-propyl-1,3-dioxolan-2-ylmethyl)-2,6-diethylaniline, N-α-chloroacetyl-N-(4,5-dimethyl-1,3-dioxolan-2-ylmethyl)-2,6-diethylaniline, N-α-chloroacetyl-N-(4,5-diethyl-1,3-dioxolan-2-ylmethyl)-2,6-diethylaniline, N-α-chloroacetyl-N-(4-methyl-1,3-dioxan-2-ylmethyl)-2,6-diethylaniline, N-α-chloroacetyl-N-(4-ethyl-1,3-dioxan-2-ylmethyl)-2,6-diethylaniline, N-α-chloroacetyl-N-(4,6-dimethyl-1,3-dioxan-2-ylmethyl)-2,6-diethylaniline, N-α-chloroacetyl-N-(4,6-diethyl-1,3-dioxan-2-ylmethyl)-2,6-diethylaniline, N-α-chloroacetyl-N-(4-hexyl-1,3-dioxan-2-ylmethyl)-2,6-diethylaniline, N-α-chloroacetyl-N-(4-methyl-1,3-dioxepan-2-ylmethyl)-2,6-diethylaniline, N-α-chloroacetyl-N-(4-ethyl-1,3-dioxepan-2-ylmethyl)-2,6-diethylaniline, N-α-chloroacetyl-N-(4,7-dimethyl-1,3-dioxepan-2-ylmethyl)-2,6-diethylaniline, N-α-chloroacetyl-N-(4-propyl-1,3-dioxepan-2-ylmethyl)-2,6-diethylaniline, N-α-chloroacetyl-N-(4-butyl-1,3-dioxepan-2-ylmethyl)-2,6-diethylaniline, N-α-chloroacetyl-N-(4-hexyl-1,3-dioxepan-2-ylmethyl)-2,6-diethylaniline, N-α-chloroacetyl-N-(1,3-dithiolan-2-ylmethyl)-2,6-dimethylaniline, N-α-chloroacetyl-N-(1,3-dithiolan-2-ylmethyl)-2,6-diethylaniline, N-α-chloroacetyl-N-(1,3-dithiolan-2-ylmethyl)-2,6-dipropylaniline, N-α-chloroacetyl-N-(1,3-dithiolan-2-ylmethyl)-2,6-dibutylaniline, N-α-chloroacetyl-N-(1,3-dithiolan-2-ylmethyl)-2,6-dipentylaniline, N-α-chloroacetyl-N-(1,3-dithiolan-2-ylmethyl)-2,6-dihexylaniline, N-α-chloroacetyl-N-(1,3-dithiolan-2-ylmethyl)-2-methyl-6-ethylaniline, N-α-chloroacetyl-N-(1,3-dithiolan-2-ylmethyl)-2-methyl-6-methoxyaniline, N-α-chloroacetyl-N-(1,3-dithiolan-2-ylmethyl)-2-methyl-6-ethoxyaniline, N-α-chloroacetyl-N-(1,3-dithiolan-2-ylmethyl)-2-methyl-6-hexyloxyaniline, N-α-chloroacetyl-N-(1,3-dithiolan-2-ylmethyl)-2-ethyl-4-chloroaniline, N-α-chloroacetyl-N-(1,3-dithiolan-2-ylmethyl)-2-ethyl-3-methylaniline, N-α-chloroacetyl-N-(1,3-dithiolan-2-ylmethyl)-2-ethyl-4-bromoaniline, N-α-chloroacetyl-N-(1,3-dithiolan-2-ylmethyl)-2-ethyl-4-fluoroaniline, N-α-chloroacetyl-N-(1,3-dithiolan-2-ylmethyl)-2-ethylaniline, N-α-chloroacetyl-N-(1,3-dithiolan-2-ylmethyl)-2-methylaniline, N-α-chloroacetyl-N-(1,3-dithiolan-2-ylmethyl)-2-propylaniline, N-α-chloro-propionyl-N-(1,3-dithiolan-2-ylethyl)-2,6-diethylaniline, N-α-bromopropionyl-N-(1,3-dithiolan-2-ylmethyl)-2,6-diethylaniline, N-α-bromoacetyl-N-(1,3-dithiolan-2-ylmethyl)-2,6-diethylaniline, N-α-chlorobutanoyl-N-(1,3-dithiolan-2-ylmethyl)-2,6-diethylaniline, N-α-chloropentanoyl-N-(1,3-dithiolan-2-ylmethyl)-2,6-diethylaniline, N-α-chloroacetyl-N-(1,3-dithian-2-ylmethyl)-2,6-diethylaniline, N-α-chloroacetyl-N-(1,3-dithian-2-ylmethyl)-2,6-dimethylaniline, N-α-chloroacetyl-N-(1,3-dithian-2-ylmethyl)-2,6-diethylaniline, N-α-chloroacetyl-N-(1,3-dithian-2-ylmethyl)-2,6-dimethylaniline, N-α-chloroacetyl-N-(1,3-dithian-2-ylmethyl)-2,6-dipropylaniline, N-α-chloroacetyl-N-(1,3-dithian-2-ylmethyl)-2-methyl-4-chloroaniline, N-α-chloroacetyl-N-(1,3-dithian-2-ylmethyl)-2,4,6-trimethylaniline, N-α-chloroacetyl-N-(1,3-dithian-2-ylmethyl)-2-methyl-4-fluoroaniline, N-α-chloroacetyl-N-(1,3-dithian-2-ylmethyl)-2-ethyl-6-methoxyaniline, N-α-chloropropionyl-N-(1,3-dithian-2-ylethyl)-2,6-diethylaniline, N-α-bromoacetyl-N-(1,3-dithian-2-ylmethyl)-2,6-diethylaniline, N-α-chlorobutanoyl-N-(1,3-dithian-2-ylmethyl)-2,6-diethylaniline, N-α-chloropentanoyl-N-(1,3-dithian-2-ylmethyl)-2,6-diethylaniline, N-α-chlorohexanoyl-N-(1,3-dithian-2-ylmethyl)-2,6-diethylaniline, N-α-chloroacetyl-N-(1,3-dithiepan-2-ylmethyl)-2,6-dimethylaniline, N-α-chloroacetyl-N-(1,3-dithiepan-2-ylmethyl)-2,6-diethylaniline, N-α-chloroacetyl-N-(1,3-dithiepan-2-ylmethyl)-2,6-dipropylaniline, N-α-chloroacetyl-N-(1,3-dithiepan-2-ylmethyl)-2,6-dihexylaniline, N-α-chloroacetyl-N-(1,3-dithiepan-2-ylmethyl)-2-methyl-4-chloroaniline, N-α-chloroacetyl-N-(1,3-dithiepan-2-ylmethyl)-2-ethyl-4-fluoroaniline, N-α-chloroacetyl-N-(1,3-dithiepan-2-ylmethyl)-2-ethyl-3-butylaniline, N-α-chloroacetyl-N-(1,3-dithiepan-2-ylmethyl)-2,4,6-triethylaniline, N-α-chloroacetyl-N-(1,3-dithiepan-2-ylmethyl)-2-ethyl-6-methoxyaniline, N-α-chloroacetyl-N-(1,3-dithiepan-2-ylmethyl)-2,6-diethyl-4-bromoaniline, N-α-bromoacetyl-N-(1,3-dithiepan-2-ylmethyl)-2,6-diethylaniline, N-α-chloropropionyl-N-(1,3-dithiepan-2-ylmethyl)-2,6-diethylaniline, N-α-bromopropionyl-N-(1,3-dithiepan-2-ylmethyl)-2,6-diethylaniline, N-α-chlorobutanoyl-N-(1,3-dithiepan-2-ylethyl)-2,6-diethylaniline, N-α-chloropentanoyl-N-(1,3-dithiepan-2-ylethyl)-2,6-diethylaniline, N-α-chloroacetyl-N-(4-methyl-1,3-dithiolan-2-ylmethyl)-2,6-diethylaniline, N-α-chloroacetyl-N-(4-ethyl-1,3-dithiolan-2-ylmethyl)-2,6-diethylaniline, N-α-chloroacetyl-N-(4-propyl-1,3-dithiolan-2-ylmethyl)-2,6-diethylaniline, N-α-chloroacetyl-N-(4,5-dimethyl-1,3-dithiolan-2-ylmethyl)-2,6-diethylaniline, N-α-chloroacetyl-N-(4,5-diethyl-1,3-dithiolan-2-ylmethyl)-2,6-diethylaniline, N-α-chloroacetyl-N-(4-methyl-1,3-dithian-2-ylmethyl)-2,6-diethylaniline, N-α-chloroacetyl-N-(4-ethyl-1,3-dithian-2-ylmethyl)-2,6-diethylaniline, N-α-chloroacetyl-N-(4,6-dimethyl-1,3-dithian-2-ylmethyl)-2,6-diethylaniline, N-α-chloroacetyl-N-(4,6-diethyl-1,3-dithian-2-ylmethyl)-2,6-diethylaniline, N-α-chloroacetyl-N-(4-hexyl-1,3-dithian-2-ylmethyl)-2,6-diethylaniline, N-α-chloroacetyl-N-(4-methyl-1,3-dithiepan-2-ylmethyl)-2,6-diethylaniline, N-α-chloroacetyl-N-(4-ethyl-1,3-dithiepan-2-ylmethyl)-2,6-diethylaniline, N-α-chloroacetyl-N-(4,7-dimethyl-1,3-dithiepan-2-ylmethyl)-2,6-diethylaniline, N-α-chloroacetyl-N-(4-propyl-1,3-dithiepan-2-ylmethyl)-2,6-diethylaniline, N-α-chloroacetyl-N-(4-butyl-1,3-dithiepan-2-ylmethyl)-2,6-diethylaniline and N-α-chloroacetyl-N-(4-hexyl-1,3-dithiepan-2-ylmethyl)-2,6-diethylaniline.

Exemplary compounds of formula II are N,N-diallyldichloroacetamide, N-ethyl-N-allyldichloroacetamide, N-dichloroacetyl-2,2-dimethyl-1,3-oxazolidine, N-isopropyl-N-allyldichloroacetamide, N-(2-methylprop-2-enyl)-N-n-propyldichloroacetamide, N-(1-cyanoethyl)-N-n-propyldichloroacetamide, N-(2-methylprop-2-enyl)-N-(3-methoxypropyl)dichloroacetamide, N,N-di-sec-butyldichloroacetamide, N-(2-methylprop-2-enyl)-N-allyldichloroacetamide, N-propargyl-N-allyldichloroacetamide, N-(2-chloroallyl)-N-allyldichloroacetamide, N-(2-methylprop-2-enyl)-N-t-butyldichloroacetamide, N-cyclohexyl-N-isopropyldichloroacetamide N-(2-chloroallyl)-N-ethyldichloroacetamide, N-propargyl-N-n-propyldichloroacetamide, N,N-di-(2-methylprop-2-enyl)dichloroacetamide, N-but-2-enyl-N-ethyldichloroacetamide, N-(2,3-dichloropropyl)-N-ethyldichloroacetamide, N-cyclopropyl-N-allyldichloroacetamide, N-(1-cyanoethyl)-N-allyldichloroacetamide, N-allyl-N-(2-chloroallyl)dichloroacetamide, N,N-di-(3-chloroprop-2-enyl)dichloroacetamide, N-(3-chloroprop-2-enyl)-N-isopropyldichloroacetamide, N-(3-chloroprop-2-enyl)-N-methyldichloroacetamide, N-allyl-N-n-propyldichloroacetamide, N-allyl-N-methyldichloroacetamide, N-propargyl-N-ethyldichloroacetamide, N-cyanomethyl-N-methyldichloroacetamide and N-(1,1-dimethylethynyl)-N-ethyldichloroacetamide.

As previously indicated, the compositions of the present invention, comprising in combination compounds of formulae I and II, are useful in destroying weeds in the cultivation of cereal grains without causing damage to said grain plants. The compositions of this invention are particularly suited in controlling weeds in the cultivation of corn.

For practical use as herbicides the combination of compounds of this invention are generally incorporated into herbicidal compositions which comprise an inert carrier and a herbicidally toxic amount of such a compound. Such herbicidal compositions, which can also be called formulations, enable the active compounds to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compounds with a solid inert carrier such as the talcs, clays, silicas, pyrophyllite, and the like. Granular formulations can be prepared by impregnating the compounds, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compounds, can be prepared by incorporating wetting agents into concentrated dust compositions.

In some cases the active compounds are sufficiently soluble in common organic solvents such as kerosene or xylene so that they can be used directly as solutions in these solvents. Frequently, solutions can be dispersed under superatmospheric pressure as aerosols. However, preferred liquid herbicidal compositions are emulsifiable concentrates, which comprise a combination of compounds according to this invention and as the inert carrier, a solvent and an emulsifier. Such emulsifiable concentrates can be extended with water and/or oil to any desired concentration of active compounds for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

The compositions of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, the combination of compounds of the present invention. The concentration of the active combination of compounds of this invention in the herbicidal compositions will vary greatly with the type of formulation and the purpose for which it is designed, but generally the herbicidal compositions will comprise from about 0.05 to about 95 percent by weight of the active combination of compounds of this invention. In a preferred embodiment of this invention, the herbicidal compositions will comprise from about 5 to about 75 percent by weight of the active combination of compounds. The compositions can also comprise such additional substances as other pesticides, such as insecticides, nematocides, fungicides, and the like; stabilizers, spreaders, deactivators, adhesives, stickers, fertilizers, activators, synergists, and the like.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose-grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, winter-cress, horsenettle, nutsedge, milkweed and sicklepod.

Similarly, such weeds can be classified as broadleaf or grassy weeds. It is economically desirable to control the growth of such weeds without damaging beneficial plants or livestock.

The new compositions of this invention are particularly valuable for weed control because they are toxic to many species and groups of weeds while they are relatively non-toxic to cereal grains and particularly corn. The exact amount of active compounds required will depend on a variety of factors, including the hardiness of the particular weed species, weather, type of soil, method of application, the kind of beneficial plants in the same area, and the like. Thus, while the application of up to only about one or two ounces of active compounds per acre may be sufficient for good control of a light infestation of weeds growing under adverse conditions, the application of ten pounds or more of active compounds per acre may be required for good control of a dense infestation of hardy perennial weeds growing under favorable conditions.

Some typical herbicidal compositions which can be used in controlling weeds in cereal grains in accordance with the present invention are shown in the following examples in which all quantities are in parts by weight.

EXAMPLE 1

Preparation of a Wettable Powder

The following components are mixed intimately in conventional mixing or blending equipment and are then ground to a powder having an average particle size of less than about 50 microns. The finished powder is then dispersed in water to give the desired concentration of active ingredients.

| | |
|---|---|
| N-α-chloroacetyl-N-(1,3-dioxolan-2-ylmethyl)-2,6-diethylaniline | 20.0 |
| N,N-diallyldichloroacetamide | 3.0 |
| fuller's earth | 72.0 |
| sodium lauryl sulfate | 2.5 |
| methyl cellulose | 2.5 |

EXAMPLE 2

Preparation of a Wettable Powder

The following ingredients are mixed intimately in conventional mixing or blending equipment and are then ground to a desired particle size. Immediately prior to application the finished powder is dispersed in water to give the desired concentration of the combination of active compounds.

| | |
|---|---|
| N-α-chloroacetyl-N-(1,3-dioxan-2-ylmethyl)-2,6-diethylaniline | 50.0 |
| N-allyl-N-ethyldichloroacetamide | 0.005 |
| fuller's earth | 25.0 |
| sodium lauryl sulfate | 3.0 |
| methyl cellulose | 2.0 |

EXAMPLE 3

Preparation of a Dust

The following ingredients are mixed thoroughly and are then ground to an average particle size of less than about 50 microns to give a dust suitable for application with conventional dusting equipment.

| | |
|---|---|
| N-α-chloroacetyl-N-(1,3-dithiolan-2-ylmethyl)-2,6-diethylaniline | 9.0 |
| N-dichloroacetyl-2,2-dimethyl-1,3,-oxazolidine | 1.0 |
| talc | 90.0 |

EXAMPLE 4

Preparation of an Oil-dispersible Powder

The following ingredients are blended in conventional mixing equipment and are then ground to a powder having an average particle size of less than about 50 microns to give a powder which can be dispersed in oil to form a spray containing the desired concentration of active compounds.

| | |
|---|---|
| N-α-chloroacetyl-N-(1,3-dioxepan-2-ylmethyl)-2-ethyl-6-methoxyaniline | 66.0 |
| N-isopropyl-N-allyldichloroacetamide | 4.0 |
| condensation product of diamylphenol with ethylene oxide | 4.0 |
| fuller's earth | 26.0 |

EXAMPLE 5

Preparation of a Granular Formulation

The following ingredients are mixed with sufficient water to form a paste, which is then extruded, dried and ground to give granules, preferably from about 1/32 to ¼ inch diameter. The granules are applied with fertilizer spreader equipment or other conventional apparatus. The dextrin in this formulation serves as a binding agent.

| | |
|---|---|
| N-α-chloropropionyl-N-(1,3-dithian-2-ylethyl)-2-ethyl-4-chloroaniline | 10.0 |
| N-propargyl-N-allyldichloroacetamide | 0.5 |
| fuller's earth | 65.5 |
| dextrin | 20.0 |
| sodium lignin sulfonate | 3.0 |
| kerosene | 1.0 |

EXAMPLE 6

Preparation of an Emulsifiable Concentrate

The following components are mixed together until a clear solution is obtained which can then be extended with water to any desired concentration of active compound for application to the weed infestation.

| | |
|---|---|
| N-α-chloroacetyl-N-(1,3-dithiepan-2-ylmethyl)-2,6-diethyl-4-bromoaniline | 30.0 |
| N-(2-methylprop-2-enyl)-N-n-propyldichloroacetamide | 2.0 |
| blend of oil-soluble calcium sulfonates with polyoxyethylene ethers | 6.0 |
| xylene | 62.0 |

The herbicidal effectiveness of the compositions of the present invention and their safety to cereal grains such as corn can be illustrated by many of the established testing techniques known to the art such as pre- and post-emergence testing.

The herbicidal activity of the compositions of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and a test compound formulated as an aqueous emulsion of an acetone solution containing emulsifiers is sprayed at the desired concentrations on the surface of the soil.

After spraying, the soil containers are placed in the greenhouse and provided with supplementary heat as required and daily or more frequent watering. The plants are maintained under these conditions for a period of from 15 to 21 days, at which time the condition of the plants and the degree of injury to the plants is rated on a scale of from 0 to 10 as follows: 0 = no injury, 1,2 = slight injury, 3,4 = moderate injury, 5,6 = moderately severe injury, 7,8,9 = severe injury and 10 = death.

The herbicidal activity of the compounds of this invention can also be demonstrated by experiments carried out for the post-emergence control of a variety of weeds. In these experiments the compounds to be tested are formulated as aqueous emulsions and sprayed at the desired dosage on the foliage of the weeds that have attained a prescribed size. After spraying the plants are placed in a greenhouse and watered daily or more frequently. Water is not applied to the foliage of the treated plants. The severity of injury is determined 10 to 15 days after treatment and is rated on the scale of from 0 to 10 heretofore described.

I claim:

1. Herbicidal compositions which reduce injury to corn from the treatment of herbicides comprising in combination an herbicide of the formula

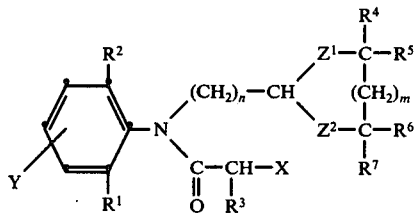

wherein Y is hydrogen; $R^1$ is lower alkyl; $R^2$ is lower alkyl; $R^3$ is hydrogen; X is chlorine; $n$ is 1; $Z^1$ and $Z^2$ are oxygen; $R^4$, $R^5$, $R^6$ and $R^7$ are hydrogen; and $m$ is 0; and from 0.01 to 15.0 weight percentage of said herbicide of an antidote for said herbicide of the formula

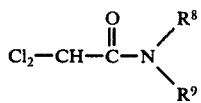

wherein $R^8$ and $R^9$ are lower alkenyl.

2. An herbicidal composition comprising an inert carrier and as an essential active ingredient in a quantity toxic to weeds, a first compound consisting of an herbicide of the formula

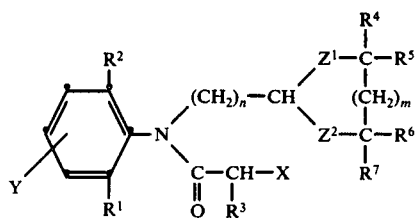

wherein Y is hydrogen; $R^1$ is lower alkyl; $R^2$ is lower alkyl; $R^3$ is hydrogen; X is chlorine; $n$ is 1; $Z^1$ and $Z^2$ are oxygen; $R^4$, $R^5$, $R^6$ and $R^7$ are hydrogen; and $m$ is 0; and from 0.01 to 15.0 weight percentage of said herbicide of an antidote for said herbicide of the formula

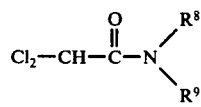

wherein $R^8$ and $R^9$ are lower alkenyl.

3. The composition of claim 2 wherein the first compound is N-α-chloroacetyl-N-(1,3-dioxolan-2-ylmethyl)-2,6-diethylaniline.

4. The composition of claim 2, wherein the first compound is N-alpha-chloroacetyl-N-(1,3-dioxolan-2-ylmethyl)-2,6-dimethylaniline.

5. A method of controlling weeds in corn which comprises contacting the locus of said weeds with a herbicidal composition of claim 2.

* * * * *